US006921643B2

(12) United States Patent
Gill et al.

(10) Patent No.: US 6,921,643 B2
(45) Date of Patent: Jul. 26, 2005

(54) COMPOSITIONS AND METHODS FOR DETECTING A SEQUENCE MUTATION IN THE CINNAMYL ALCOHOL DEHYDROGENASE GENE ASSOCIATED WITH ALTERED LIGNIFICATION IN LOBLOLLY PINE

(75) Inventors: Geoffrey P. Gill, Davis, CA (US); Garth R. Brown, Davis, CA (US); David B. Neale, Davis, CA (US)

(73) Assignees: The Regents of the University of California, Oakland, CA (US); The United States of America as represented by the Secretary of Agriculture, Washington, DC (US)

(*) Notice: Subject to any disclaimer, the term of this patent is extended or adjusted under 35 U.S.C. 154(b) by 313 days.

(21) Appl. No.: 10/359,451

(22) Filed: Feb. 5, 2003

(65) Prior Publication Data

US 2004/0152086 A1 Aug. 5, 2004

(51) Int. Cl.[7] .......................... C07H 21/04; C12Q 1/68

(52) U.S. Cl. ......................... 435/6; 435/91.1; 435/91.2; 536/23.1

(58) Field of Search .......................... 435/6, 91.1, 91.2; 536/23.1

(56) References Cited

U.S. PATENT DOCUMENTS

| | | | |
|---|---|---|---|
| 5,451,514 | A | 9/1995 | Boudet et al. |
| 5,633,439 | A | 5/1997 | Walter |
| 5,824,842 | A | 10/1998 | MacKay et al. |
| 6,015,943 | A | 1/2000 | Boudet et al. |
| 6,066,780 | A | 5/2000 | Boudet et al. |
| 6,395,204 | B1 | 5/2002 | Neogi et al. |

FOREIGN PATENT DOCUMENTS

| | | |
|---|---|---|
| WO | WO 93/05159 | 3/1993 |
| WO | WO 93/24638 | 12/1993 |
| WO | WO 99/07865 | 2/1999 |
| WO | WO 01/95702 A1 | 12/2001 |
| WO | WO 02/052035 A2 | 7/2002 |

OTHER PUBLICATIONS

Wu et al. Theor Appl genet. vol. 99, pp. 705–710, 1999.*

MacKay "A mutation in lignin biosynthesis in loblolly pine; genetic molecular and biochemical analyses" PhD thesis. North Carolina State University, Raleigh, NC, 1996.*

Gill, Geoffrey P., et al., "A Sequence Mutation in the Cinnamyl Alcohol Dehydrogenase Gene Associated with Altered Lignification in Loblolly Pine" *Plant Biotechnology Journal* (2003) 1, pp. 253–258.

*Anonymous*, "On the trail of the mutant pine" *Chemistry and Industry* (*London*) No. 14, Jul. 21, 1997: 543.

Boudet, A.M. et al. "Developmental and stress lignification": conference paper from "*Eurosilva*: contribution to forest tree physiology" Final Workshop, Eurosilva Research Programme, Dourdan, France, Nov. 7–10, 1994: 13–14.

Boudet, A.M. "Des lignines sure mesure" *Biofutur* No. 172, 1997, pp. 58–59. (English Abstract).

Feuillet, C. et al. "Nucleotide sequence of a cDNA encoding cinnamyl alcohol dehydrogenase from Eucalyptus" *Plant Physiology* 103 (4), 1993: 1447.

Galliano, H. et al. "Molecular cloning, sequence analysis and elicitor–/ozone–induced accumulation of cinnamyl alcohol dehydrogenase from Norway spruce" *Plant Molecular Biology*23 (1), 1993: 145–146.

Li, XinGuo et al. "Single nucleotide polymorphisms (SNPs) detection on base sequences of CAD gene in lignin biosynthesis of loblolly pine" *Journal of Beijing Forestry University* 23 (6), 2001: 5–9.

MacKay, J.J. et al. "Genetic Analysis of cinnamyl alcohol dehydrogenase in loblolly pine: single gene inheritance, molecular characterization and evolution" *Molecular and General Genetics* 247 (5), 1995: 537–545.

MacKay, J.J. "A Mutation in Lignin Biosynthesis in Loblolly Pine: Genetic, Molecular and Biochemical Analyses" *Thesis: Graduate School of North Carolina State University*, 1996: 1–144.

MacKay, John J. et al. "Inheritance, gene expression, and lignin characterization in a mutant pine deficient in cinnamyl alcohol dehydrogenase" *Proc. Natl. Acad. Sci. USA* 94, Jul. 1997: 8255–8260 (online from http://www.pnas.org/cgi/content/full/94/15/8255, Dec. 5, 2002.

MacKay, J. et al. "Modified lignin and delignification with a CAD–deficient loblolly pine" *Holzforschung* 53 (4), 1999: 403–410.

O'Malley, D.M. et al. "Purification, characterization, and cloning of cinnamyl alcohol dehydrogenase in loblolly pine" *Plant Physiology* 98 (4), 1992: 1364–1371.

(Continued)

*Primary Examiner*—Jeanine A. Goldberg
(74) *Attorney, Agent, or Firm*—Morrison & Foerster LLP

(57) ABSTRACT

Loblolly pine (*Pinus taeda* L.) is the most important commercial tree species in the USA harvested for pulp and solid wood products. Increasing the efficiency of chemical pulping may be achieved through the manipulation of genes involved in the lignin biosynthetic pathway. A null allele of cinnamyl alcohol dehydrogenase (CAD) has been discovered in the loblolly pine clone 7-56 which displays altered lignin composition. During identification of single nucleotide polymorphisms (SNPs) in the cad gene, a two-base pair adenosine insertion located in exon five and unique to clone 7-56 was discovered. The sequence mutation causes a frame-shift predicted to result in premature termination of the protein. For routine detection of the mutation, a diagnostic assay was developed utilising Template-directed Dye-terminator Incorporation and Fluorescence Polarization detection (FP-TDI).

48 Claims, 3 Drawing Sheets

OTHER PUBLICATIONS

Schubert, R. et al. "The cinnamyl alcohol dehydrogenase gene structure in Picea abies Karst.: genomic sequences, Southern hybridization, genetic analysis and phylogenetic relationships" *Trees: Structure and Function* 12 (8), 1998: 453–463.

Sederoff, R. "Genetic regulation of lignin biosynthesis and the potential modification of wood by genetic engineering in loblolly pine" *Genetic Engineering of plant secondary metabolism* 1994: 313–355.

Sederoff, R.R. et al. "Unexpected variation in lignin" *Current Opinion in Plant Biology* 2 (2), 1999: 145–152.

Wu, R. L. et al. "Average effect of a mutation in lignin biosynthesis in loblolly pine" *Theor Appl Genet* 99, 1999: 705–710.

* cited by examiner

```
                codon
Forward assay   240
                 ↓
     wild type  [G A A]- -[G C A|G C A|G A G|A G C|C T A]    SEQ ID NO:5
                        [C T T|C G T|C G T|C T C|T C G|G A T]    SEQ ID NO:6

     csd-n1     [G A A|A A G|C A G|C A G|A G A|G C C|T A G]    SEQ ID NO:7
                        [C T T|T T C|G T C|G T C|T C T|C G G|A T C]    SEQ ID NO:8

Reverse assay
     wild type  [G A A]- -[G C A|G C A|G A G|A G C|C T A]    SEQ ID NO:5
                        [C T T|C G T|C G T|C T C|T C G|G A T]    SEQ ID NO:6

     csd-n1     [G A A|A A G|C A G|C A G|A G A|G C C|T A G]    SEQ ID NO:7
                        [C T T|T T C|G T C|G T C|T C T|C G G|A T C]    SEQ ID NO:8
```

COMPOSITIONS AND METHODS FOR DETECTING A SEQUENCE MUTATION IN THE CINNAMYL ALCOHOL DEHYDROGENASE GENE ASSOCIATED WITH ALTERED LIGNIFICATION IN LOBLOLLY PINE

GOVERNMENT INTEREST

This invention was made with United States support under Grant No. 9975806 awarded, by the National Science Foundation. The United States has certain rights in the invention.

FIELD OF THE INVENTION

This invention is in the field of pine tree breeding and selection. In particular, this invention relates to methods and compositions for identifying pine trees that harbor the null cinnamyl alcohol dehydrogenase (CAD) allele (cad-n1).

BACKGROUND OF THE INVENTION

Global consumption of wood products is projected to increase 25% over current levels by 2015 (McLaren 1999). Full citations for the references cited herein are provided before the claims. Forest plantations are increasingly important to meet these global demands because their faster growth rates result in much more harvestable volume per unit area than natural forests (Hagler 1996, Sedjo 1999). Thus, reliance on plantations reduces the need to harvest natural forests, allowing them to be used for other societal purposes. In fact, as little as 5 to 10% of the total area of world's forests would be required to meet global demands for wood products if this area were devoted to fast-growing plantations (Hagler 1996, Sedjo and Botkin 1997). Further, the faster growth rates mean high rates of carbon sequestration that may mitigate the effects of global warming. These facts, coupled with the declining area available for commercial forest harvests due to deforestation and government restrictions, have led to a global effort to increase plantation growth rates per unit area above current values through both classical and new technologies (Fox 2000).

Viewed as an agricultural crop, timber is the single highest-valued crop in the USA and loblolly pine (*Pinus taeda* L) is the most important commercial tree species in the USA. Each year more than 900 million seedlings are used to establish loblolly pine plantations on more than half a million hectares (Pye et al. 1997). The total acreage of the loblolly pine plantation estate is estimated at more than 12 million hectacres (Byram et al. 1999). Loblolly pine is also important for its ecological and biological importance in native forests. Its native range spans 14 states from southern New Jersey south to central Florida and west to Texas. In these natural forests it is the dominant tree species on 11.7 million ha (Baker and Langdon 1990). Thus, loblolly pine is nearly equal in its distribution between native and planted forests totaling 23.7 million hectares. By comparison, the total expanse of plantations of hybrid poplar in the Pacific Northwest is approximately 25,000 ha (Nuss 1999), which is only 0.2% of the area planted in loblolly pine.

Due to its overwhelming commercial importance, tree breeding programs for loblolly pine began in the 1950's, and virtually all forest products companies and state agencies are involved in genetic improvement programs (more than 30 organizations) (Byram et al. 1999, Li et al. 1999). These programs have used classical methods of selection, genetic testing and breeding to make demonstrable genetic progress.

Unfortunately the progress is hindered, compared to that in agricultural crops, by the large size and long-lived nature of pines (eight years in field tests to make selections followed by another five or more years to complete breeding). For these reasons, most loblolly pine programs are only in their second or third cycle of breeding after nearly 50 years, when in some crops more than one cycle is completed in a single year.

Loblolly pine (*Pinus taeda* L.) is the most intensively grown tree species in the USA for pulp and solid wood products with plantations exceeding 12 million hectares. The extraction of lignin from wood during the production of pulp and paper requires the use of costly chemicals that are toxic to the environment. Significant progress towards increasing pulping efficiency has been achieved in poplar through the genetic manipulation of genes involved in lignin biosynthesis (Baucher et al., 1996, Hu et al., 1999; Pilate et al., 2002). One of the key enzymes successfully targeted, cinnamyl alcohol dehydrogenase (CAD), catalyzes the final step in the synthesis of monolignols by converting cinnamaldehydes to cinnamyl alcohols. Field-grown transgenic poplar with reduced-CAD allowed easier delignification, using smaller amounts of chemicals and yielded more high quality pulp without an adverse effect on growth (Pilate et al., 2002).

A null CAD allele (cad-n1) has been discovered in the loblolly pine clone 7-56 which is heterozygous for the null allele (MacKay et al., 1997). Homozygous seedlings (cad-n1/cad-n1) obtained by selfing, contain between 0–1% of wild type CAD activity (MacKay et al., 1997) and display a brown-red wood phenotype. The expression level of cad transcript in shoot, megagametophyte and xylem tissues was 20 times less in cad-n1 homozygous plants compared to wild type (MacKay et al., 1997).

Deficiency of CAD in cad-n1 homozygotes only slightly reduces lignin content but drastically alters lignin composition (MacKay et al., 1997; Ralph et al., 1997; Lapierre et al., 2000; MacKay et al., 2001). The major lignin composition change was attributed to the incorporation of dihydroconiferyl alcohol (DHCA), a minor component of most lignins, but elevated to levels 10-fold higher in cad-n1 homozygous trees. Coniferaldehyde, the substrate of CAD, and vanillin are also present in increased levels while the coniferyl alcohol component of normal lignin decreased.

The mutation has a variable effect on pulping efficiency, depending on the age of the trees and whether the mutation is present in a homozygous or heterozygous state. In totally CAD-deficient trees (cad-n1/cad-n1), delignification was significantly easier but the pulp yields were relatively low (~33%) compared to normal trees (48%) (Dimmel et al., 2001). In 4–6 year old partially CAD-deficient trees (heterozygous) delignification increased in efficiency by ~20% and yields were similar to wild type (Dimmel et al., 2002). In contrast to these younger trees, a small sample of 14 year old partially CAD-deficient trees displayed no major differences in ease of delignification and pulp yield (Dimmel et al., 2002).

In addition to lignin composition changes, the cad-n1 allele appears to be associated with increased stem-growth traits in heterozygous trees (Wu et al., 1999). This growth promotion correlates to an increase in debarked volume of 4-year old trees (14%) (Wu et al., 1999) that is also observed in 14-year old trees (Dimmel et al., 2002). A likely explanation could be that trees harboring the cad-n1 allele may invest fewer resources into the production of monolignols, allowing reallocation of resources towards growth. Promotion of growth was also observed in transgenic poplar with the lignin biosynthetic enzyme 4-coumarate:coenzyme A ligase (4CL) down-regulated (Hu, et al., 1999).

For the above reasons, it is desirable to be able to select pine trees that harbor the null CAD allele (cad-n1). Traditionally, the mutation has been diagnosed using CAD isozyme analysis on haploid megagametophytes obtained from seed or by using genetic markers closely linked to the mutation (MacKay et al., 1997). These prior art methods are slow and tedious. It takes numerous years for pine tree seedlings to produce suitable seed for CAD isozyme marker analysis. In addition, linked genetic marker analysis is slow and often yields inaccurate results. There is thus a tremendous need to develop methods that allow rapid and accurate identification of pine trees that harbor the null CAD allele (cad-n1).

SUMMARY OF THE INVENTION

In order to meet these needs, the present invention relates to the identification of a sequence mutation responsible for the loss of function associated with the cad-n1 allele. This mutation was identified during single nucleotide polymorphism (SNP) discovery within the cad gene of loblolly pine. Identification of this mutation allows breeders to accurately determine the presence, absence and/or copy number of the cad-n1 allele in their germplasm before it reaches sexual maturity.

The present invention is directed to a method of identifying a loblolly pine tree harboring a null CAD allele (cad-n1) wherein the pine tree contains a cad gene and the cad gene has a fifth exon. A pine tree is said to "harbor" or contain the null CAD allele if it is homozygous for the null CAD allele (cad-n1/cad-n1) or is heterozygous for the null CAD allele (cad-n1/cad). Pine trees that are homozygous for the wild type CAD allele (cac/cad) do not harbor the null CAD allele. This sequence differs from the wild type sequence of the fifth exon of the cad gene depicted in SEQ ID NO:1. It is expected that there will be some genetic variation in the wild type cad gene sequence resulting in slight differences in the wild type sequence compared to SEQ ID NO:1.

In one format, the method includes identifying a pine tree containing a two base pair adenosine insertion in the fifth exon of the cad gene wherein the DNA sequence of the two base pair adenosine insertion includes the nucleotide sequence depicted in SEQ ID NO:3 or the complement thereof.

The present invention is further directed to a method of selecting a loblolly pine tree harboring a null CAD allele (cad-n1) wherein the pine tree contains a cad gene and the cad gene has a fifth exon. The method includes a) providing a sample including DNA from the pine tree wherein the DNA includes the cad gene; b) determining whether the fifth exon contains a two base pair adenosine insertion wherein the nucleotide sequence of the fifth exon containing the two base pair adenosine insertion includes the nucleotide sequence depicted in SEQ ID NO:3 or the complement thereof wherein the identification of the two base pair adenosine insertion is indicative of a pine tree harboring a null CAD allele (cad-n1) and c) identifying a sample containing the two base pair adenosine insertion to thereby select a loblolly pine tree harboring a null CAD allele (cad-n1).

The present invention is further directed to a method of identifying a loblolly pine tree harboring a null CAD allele (cad-n1) wherein the method includes a) providing a sample including DNA from the pine tree wherein the DNA contains a cad gene and the cad gene has a fifth exon; b) performing template-directed dye-terminator incorporation and fluorescence polarization detection (FP-TDI) on the DNA to determine whether the fifth exon in the sample contains a two base pair adenosine insertion wherein the nucleotide sequence of the fifth exon containing the two base pair adenosine insertion includes the nucleotide sequence depicted in SEQ ID NO:3 wherein the two base pair adenosine insertion is indicative of a pine tree harboring a null CAD allele (cad-n1) and c) selecting a sample containing the two base pair adenosine insertion in the cad gene to thereby identify a loblolly pine tree harboring a null CAD allele (cad-n1).

The present invention is further directed to a method of identifying a loblolly pine tree harboring a null CAD allele (cad-n1) by first providing a sample including DNA from the pine tree wherein the DNA contains a cad gene and the cad gene has a fifth exon wherein the DNA in the sample is amplified by PCR using PCR primers wherein the sequences of the primers is SEQ ID NO:11 and SEQ ID NO:12. Next, template-directed dye-terminator incorporation and fluorescence polarization detection (FP-TDI) is performed on the DNA using oligonucleotides having nucleotide sequences SEQ ID NO:1 3 and SEQ ID NO:14 to determine whether the fifth exon of the cad gene in the sample contains a two base pair adenosine insertion wherein the nucleotide sequence of the fifth exon containing the two base pair adenosine insertion includes the nucleotide sequence depicted in SEQ ID NO:3 wherein the two base pair adenosine insertion is indicative of a pine tree harboring the null CAD allele (cad-n1). Finally, samples are selected containing the two base pair adenosine insertion in the cad gene to thereby identify a loblolly pine tree harboring a null CAD allele (cad-n1).

The present invention is further directed to a method of identifying a loblolly pine tree homozygous for the null CAD allele (cad-n1/cad-n1) wherein the pine tree contains a cad gene and the cad gene has a fifth exon, by identifying a pine tree, wherein the pine tree contains DNA with a two base pair adenosine insertion in the fifth exon of the cad gene wherein the DNA sequence of the two base pair adenosine insertion includes the nucleotide sequence depicted in SEQ ID NO:3 or the complement thereof. In this format, the selected pine tree does not contain DNA with wild type sequence for the fifth exon of the cad gene wherein the wild type sequence is depicted in SEQ ID NO:1.

The present invention is further directed to a method of identifying a loblolly pine tree heterozygous for the null CAD allele (cad/cad-n1) wherein the pine tree contains a cad gene and the cad gene has a fifth exon, by identifying a pine tree, wherein the pine tree contains DNA with a two base pair adenosine insertion in the fifth exon of the cad gene wherein the DNA sequence of the two base pair adenosine insertion includes the nucleotide sequence depicted in SEQ ID NO:3 or the complement thereof. In this format, the pine tree also contains wild type sequence for the fifth exon of the cad gene wherein the wild type sequence is depicted in SEQ ID NO:1 or the complement thereof.

The present invention is further directed to a method of identifying a loblolly pine tree homozygous for the wild type CAD allele (cad/cad) wherein the pine tree contains a cad gene and the cad gene has a fifth exon by identifying a pine tree, wherein the pine tree lacks DNA with a two base pair adenosine insertion in the fifth exon of the cad gene wherein the DNA sequence of the two base pair adenosine insertion includes the nucleotide sequence depicted in SEQ ID NO:3 or the complement thereof to thereby identify a pine tree homozygous for the wild type CAD allele (cad/cad).

In the methods of the invention, the identifying step may be performed on a sample isolated from a pine tree, a pine tree seedling, a pine tree tissue culture, a pine tree cell culture or a pine tree megagametophte. The sample may also be from pine bark, pine needle, pine tissue or pine seed.

In the methods of the invention, the two base pair adenosine insertion may be identified by any genotyping assay that relies on the detection of the presence or absence of the double adenosine insertion mutation. Such methods include DNA sequencing, PCR assays and single base pair extension assays.

The single base pair extension assay may be template-directed dye-terminator incorporation and fluorescence polarization detection (FP-TDI).

In one format of the invention, the FP-TDI assay may include the use of oligonucleotides wherein the sequences of the oligonucleotides are SEQ ID NO:13 or SEQ ID NO:14. The FP-TDI assay may also include the use of PCR to amplify DNA prior to the FP-TDI assay. In the PCR assay, oligonucleotides such as those depicted in SEQ ID NO:11 and SEQ ID NO:12 may be utilized.

The present invention is further directed to an isolated oligonucleotide having a nucleotide sequence selected from SEQ ID NO:9, SEQ ID NO:10, SEQ ID NO:11, SEQ ID NO:12, SEQ ID NO:13, SEQ ID NO:14.

In another format, the present invention is directed to a kit for the detection of the null CAD allele (cad-n1) in loblolly pine. The kit may include an oligonucleotide such as SEQ ID NO:13 or SEQ ID NO:14.

The kit may further include materials to perform PCR reactions. Such materials to perform PCR reactions may include PCR primers such as those depicted in SEQ ID NO:11 and SEQ ID NO:12. The kit may further include one or more buffers. The kit may also include directions for using the kit.

DETAILED DESCRIPTION OF THE INVENTION

Loblolly pine clone 7-56 is heterozygous for the null cad allele (cad/cad-n1) (MacKay et al., 1997). Selfing of these heterozygous 7-56 clones produce 25% homozygous mutant seedlings: (cad-n1/cad-n1), 50% heterozygous seedlings (cad/cad-n1) and 25% homozygous wild type seedlings: (cad/cad). The homozygous cad-n1 seedlings contain between 0–1% of wild type CAD activity. Field-grown transgenic poplar with reduced-CAD allows for easier delignification, using smaller amounts of chemicals and yields more high quality pulp without an adverse effect on growth. As such, loblolly pine tree breeders have a stong interest in being able to rapidly identify such cad-n1 homozygous plants. It would be particularly useful if a mutation in the cad gene could be identified that was associated with the reduced CAD activity in homozygous plants. Identification of such a mutation would enable the use of various rapid molecular genetic assays for the identification of (cad-n1/cad-n1), (cad/cad-n1) and (cad/cad) trees and seedlings. The present invention is directed to methods and compositions useful for indentifying and distinguishing (cad-n1/cad-n1), (cad/cad-n1) and (cad/cad) trees and seedlings.

Figure 1:
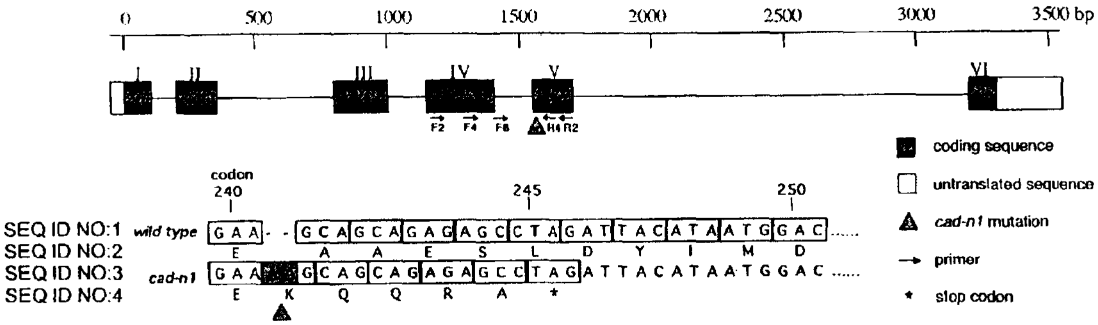
FIG. 1 shows the position of the cad-n1 sequence mutation within the cad gene and the effect of the frame-shift on amino acid sequence. A portion of the wild type cad DNA sequence is depicted as SEQ ID NO:1 with the corresponding amino acid sequence depicted as SEQ ID NO:2. A portion of the cad-n1 DNA sequence is depicted as SEQ ID NO:3 with the corresponding amino acid sequence depicted as SEQ ID NO:4.

As discussed in the Example, SNP discovery within the cad gene was performed on haploid megagametophyte DNA from clone 7-56 and 31 other unrelated individuals. A two-base pair adenosine insertion was identified unique to clone 7-56, known to be deficient in CAD activity. The insertion was located in the second codon of exon five and creates a frame-shift that generates a premature stop codon (FIG. 1). Seventeen haploid megagametophytes from the heterozygous 7-56 clone were assayed by isozyme gel electrophoresis and DNA sequence analysis to confirm the sequence mutation discovered was associated with CAD-deficiency. In every case, the two-base pair adenosine insertion corresponded with the absence of CAD activity and therefore provides a means for rapidly identifying and distinguishing (cad-n1/cad-n1), (cad/cad-n1) and (cad/cad) trees and seedlings.

Plants homozygous for the null cad allele (cad-n1/cad-n1) will contain DNA having the two base adenosine insertion in the fifth exon of the cad gene (at positions 4 and 5 of SEQ ID NO:3) but will not contain wild type DNA for the fifth exon of the cad gene as depicted in SEQ ID NO:1. As such, these plants harbor or contain the null CAD allele but do not harbor or contain the wild type CAD allele.

Plants homozygous for the wild type cad allele (cad/cad) will not contain DNA having the two base adenosine insertion in the fifth exon of the cad gene (at positions 4 and 5 of SEQ ID NO:3) but will instead only contain wild type DNA for the fifth exon of the cad gene as depicted in SEQ ID NO:1. Such plants do not harbor or contain the null CAD allele but do harbor the the wild type CAD allele.

Plants heterozygous for the null cad allele (cad-n1/cad) will contain DNA having the two base adenosine insertion in the fifth exon of the cad gene (at positions 4 and 5 of SEQ ID NO:3) and will also contain wild type DNA for the fifth exon of the cad gene as depicted in SEQ ID NO:1. As such, these plants harbor both the null CAD allele and the wild type CAD allele.

The two-base pair adenosine insertion (at positions 4 and 5 of SEQ ID NO:3) or lack thereof (the wild type sequence, SEQ ID NO:1) can be rapidly identified by numerous methods well known to those of skill in the art. Such methods include any genotyping assay that relies on the detection of the presence or absence of the double adenosine insertion mutation. Such methods include but are not limited to PCR amplification reactions, single base extension assays, primer extension assays, DNA sequencing assays and assays utilizing molecular probes [i.e. Taqman & Fluorescence Resonance Energy Transfer, (FRET)] assays and other techniques.

Figure 2:
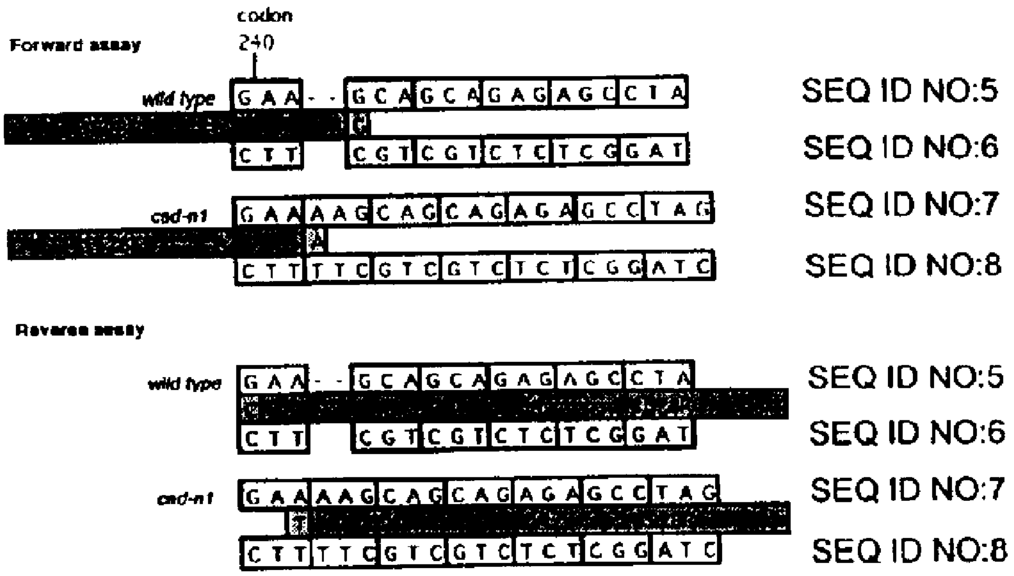
FIG. 2 shows a single base extension assay design for both the forward and reverse reactions. Forward (1528F) and reverse (1528R) assay primer positions and the corresponding fluorescent dideoxynucleotide terminator incorporated for the wild type and cad-n1 allele are also depicted. The sequences depicted in the figure are SEQ ID NO:5, SEQ ID NO:6, SEQ ID NO:7 and SEQ ID NO:8.

Primer extension is a simple, robust technique for analyzing single nucleotide polymorphisms (SNPs) such as the two base pair adenosine insertion in SEQ ID NO:3 or the complement thereof. This process is illustrated in FIG. 2 and in the Example. A primer with its 3' end directly flanking the SNP is annealed to the amplified target and induced to extend by a single ddNTP complementary to the polymorphic base. Based on the molecular weight difference between ddNTPs, extension products vary in weight depending on the incorporated nucleotide. Such extension products can be correlated and identified with a particular sequence and then utlized to detect the particular sequence.

DNA sequencing is a technique utilized to determine the sequence of nucleotides in a particular DNA molecule such as the presence or absence of the two base pair adenosine insertion in SEQ ID NO:2. Typical sequencing reactions include appropriate sequencing buffers, nucleotides, dideoxy nucleotides, DNA polymerase and one or more oligonucleotide primers. Clones containing the 5th exon of the cad gene can be sequenced with sequencing primers that flank the cloned insert, e.g. T7 polymerarse primers. Alternatively, PCR products containing the 5th exon of the cad gene, prepared, for example, as described below, can be sequenced directly.

The polymerase chain reaction (PCR) is a technique utilized to amplify DNA and can be utlized to detect differences in sequences such as the two base pair adenosine insertion in SEQ ID NO:3 of the complement thereof. Typical PCR reactions include appropriate PCR buffers, nucleotides, DNA polymerase and one or more oligonucleotide primers. Any primer amplifying exon 5 of the cad gene can be utilized. Such primers can be designed by procedures well known in the art, for example those procedures described on the UK Human Genome Mapping Project Resource Centre web site. The primers may be located within 3000 base pairs of exon 5 in pine DNA. Generally, primers should be at least 18 nucleotides in length to minimize the chances of encountering problems with a secondary hybridization site on the vector or insert. Primers with long runs of a single base should generally be avoided. It is generally important to avoid 4 or more G's or C's in a row. For cycle sequencing, primers with melting temperatures in the range 52–58 degrees C., as determined by the (A+T)2+(C+G)4 method, generally produce better results than primers with lower melting temperatures. Primers with melting temperatures above 65 degrees C. should also be avoided because of potential for secondary annealing. If the template is a high "G-C" templates, then a primer with a Tm in the 60–70 degrees C. range may be desirable. It is then advisable to do the sequencing reaction with annealing and extension at 60 C. Primers generally have a G/C content between 40 and 60 percent. For primers with a G/C content of less than 50%, it may be necessary to extend the primer sequence beyond 18 bases to keep the melting temperature above the recommended lower limit of 50 degrees C. Primers should be "stickier" on their 5' ends than on their 3' ends. A "sticky" 3' end as indicated by a high G/C content could potentially anneal at multiple sites on the template DNA. A "G" or "C" is desirable at the 3' end but the first part of this rule should apply. Primers should not contain complementary (palindromes) within themselves; that is, they should not form hairpins. If this state exists, a primer will fold back on itself and result in an unproductive priming event that decreases the overall signal obtained. Hairpins that form below 50 degrees C. generally are not such a problem. Primers should generally not contain sequences of nucleotides that would allow one primer molecule to anneal to itself or to the other primer used in a PCR reactions (primer dimer formation). If possible, it is generally useful to run a computer search against the vector and insert DNA sequences to verify that the primer and especially the 8–10 bases of its 3' end are unique.

Specific PCR primers, such as those depicted as SEQ ID NO:11 and SEQ ID NO:12, may be utilized in the reaction. Reaction products can be sequenced as described above or separated by gel electrophoresis, e.g. size gel electrophoresis, to identify those pine trees harboring or not harboring the CAD null allele.

Various modifications of general DNA sequencing, PCR and primer extension techniques are possible as detailed in *Short Protocols in Molecular Biology*, 4th Edition ed. F. M. Ausubel, R. Brent, D. D. Moore, K. Struhle, Massachusetts General Hospital and Harvard Medical School (2001) *Molecular Cloning, Molecular Cloning*, Sambrook et al. (2000) both of which are hereby incorporated by reference.

While specific oligonucleotide primer sequences are described herein, it is understood that substantially identical oligonucleotide primer sequences to those described herein will also work to permit detection of the two base pair adenosine insertion in SEQ ID NO:3 or the complement thereof that is absent from SEQ ID NO:1. The term "substantially identical" oligonucleotide primer sequences means that a oligonucleotide primer comprises a sequence that has preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference oligonucleotide sequence using standard alignment programs using standard parameters.

Pine Tree Plant Material

The two base pair mutation identifying the mutant cad gene can be detected in pine DNA or possibly RNA from pine tissue, pine cells, or pine cellular extracts. Such pine tissue, pine cells; or pine cellular extracts can be isolated from pine trees, pine tree seedlings, pine tree cell culture material, pine tree tissue culture material, pine tree seeds, pine tree needles, bark, tissue and pine tree megagametophytes. Pine seeds, tissue and wood samples can be isolated as described in MacKay, et al. Mol. Gen. Genet. 247, 537–545 (1995) which is hereby incorporated by reference in its entirety. DNA can be extracted from pine needles and megagametophytes as described in Doyle, et al. Focus 12, 13–15 (1987) which is hereby incorporated by reference in its entirety.

Kits

The present invention is also directed to a kit for the rapid and convenient, identification of cad/cad-n1; cad/cad and cad-n1/cad-n1 pine trees. The kit may be any kit useful for detecting the presence (depicted in SEQ ID NO:3) or the absence (depicted in SEQ ID NO:1) of the two base pair adenosine insertion in the fifth exon of the CAD gene. The kit may be a primer extension kit, a PCR kit or a DNA sequencing kit. All of the kits include primers useful in the various detection assays such as those described herein. The kits would also include buffers, nucleotides and directions for use. The invention will be better understood be reference to the following non-limiting Example.

EXAMPLE

Materials and Methods

Plant Material

Four plant material sources were used for the identification and testing for the presence of the cad-n1 allele: (1) A panel of 32 loblolly pine megagametophytes (Weyerhaeuser Company Federal Way, Wash., USA), including one megagametophyte from clone 7-56, was used for SNP discovery within the cad gene, (2) 167 clones (CellFor Inc., Vancouver, BC, Canada) resulting from nine crosses, using clone 7-56 or 7-56 offspring as parents, was used for testing the FP-TDI assay, (3) A selection of 242 first-generation clones (North Carolina State University Cooperative Tree Improvement Program and Weyerhaeuser Company Federal Way, Wash., USA) from the natural range of loblolly pine was used for estimating the frequency of the cad-n1 allele, and (4) 96 progeny from the VERIFICATION population (Brown et al., submitted) of the QTL pedigree (Groover et al., 1994) was used for investigating the cad-ps1 locus.

Seeds from loblolly pine clone 7-56 were germinated and the haploid megagametophytes were removed for CAD isozyme analysis or DNA extraction. CAD isozyme assays were performed as described by MacKay et al. 1995. All DNA extractions were performed using the Plant DNAeasy kit (Qiagen, Valencia, Calif., USA) in either the single tube or 96-well format.

All primers for PCR and their purpose are described in Table 1 and their relative position within the cad gene shown in FIG. 1.

nator mix (Applied Biosystems, Foster City, Calif., USA) using standard conditions as supplied by the manufacturer. Reactions were run on an ABI 377 Automated DNA sequencer using standard ABI protocols. Sequencher (GeneCodes, Ann Arbor, Mich., USA) was used to assemble sequences into a contig where polymorphic differences could be easily visualized. The cad cDNA and translated protein sequence used for alignment in this study had the genbank accession numbers Z37992 and CAA86073 respectively. The intron and exon structure of the cad gene was inferred from a *Pinus radiata* genomic sequence (AF060491).

Detection of the cad-n1 Allele using Template-directed Dye-terminator Incorporation and Fluorescence Polarization Detection (FP-TDI).

Template for the assays was amplified using the primers CADF8 and CADR2 (SEQ ID NO:1 and SEQ ID NO:12) as described in Template-directed Dye-terminator Incorporation and Fluorescence Polarization detection (FP-TDI) the PCR section. The assay design for the forward and reverse reaction is shown in FIG. 2 and the primer sequences listed in Table 1. FP-TDI reactions were performed using the Acycloprime-FP SNP detection kit (Perkin Elmer Life Sciences, Boston, Mass.) as described by the manufacturer, except thermocycling conditions were altered to 25 cycles consisting of 95° C. for 15 seconds and 54° C. for 30 seconds. Fluorescence polarization was measured on a Wallac Victor$^2$ plate reader (Perkin Elmer Life Sciences, Boston, Mass.) with the manufacturer's recommended filter sets and G-Factor calibration.

TABLE 1

Sequence of oligonucleotide primers listed by their function.

| Purpose | Forward primer | | Reverse primer | |
|---|---|---|---|---|
| Discovery (PCR and sequencing) | CADF2-CCTCTGTTATGTGCAGGGGTTACA | (SEQ ID NO:9) | CADR2-CGAAGTGCAACGGCTCTGG | (SEQ ID NO:10) |
| FP-TDI (PCR) | CADF8-TGAAAAGATGATGTGCGCCAA | (SEQ ID NO:11) | CADR2-CGAAGTGCAACGGCTCTGG | (SEQ ID NO:12) |
| FP-TDI assay | CAD1528F-ATCCGTTGTGTTGCAGGAA | (SEQ ID NO:13) | CAD1528R-GTAATCTAGGCTCTCTGCTGCTT | (SEQ ID NO:14) |

All PCR reactions were performed on ~20 ng template in a total volume of 25 μl. Each reaction comprised of 0.8 μM of each primer; 0.65 units of HotStarTaq DNA polymerase (Qiagen, Valencia, Calif., USA); 1×PCR buffer containing 1.5 mM Mg; 100 μM each of dATP, dCTP, dGTP, dTTP (Applied Biosystems, Foster City, Calif., USA). Amplification was performed on a PTC100 thermocycler (MJ Research, Waltham, Mass., USA) with the following parameters: Initial denaturation step of 95° C. for 15 min (for activation of HotStarTaq) followed by 37 amplification cycles of 30 sec at 95° C., 30 sec at 60° C. and 2 min at 72° C.

DNA Sequencing and Analysis

To provide template for sequencing, 5 μl of PCR product was treated with 1 U of exonuclease 1 (USB, Cleveland, Ohio, USA) and 1 U of shrimp alkaline phosphatase (USB, Cleveland, Ohio, USA) and incubated at 37° C. for 1 hr followed by a heat inactivation step of 85° for 15 minutes. The primers that were used during PCR were also used for sequencing (SEQ ID NO:9 and SEQ ID NO:10). Cycle sequencing was performed using ABI Prism big dye terminator mix

RESULTS AND DISCUSSION

Discovery of the cad-n1 Sequence Mutation

SNP discovery within the cad gene was performed on haploid megagametophyte DNA from clone 7-56 and 31 other unrelated individuals. A two-base pair adenosine insertion was identified unique to clone 7-56, known to be deficient in CAD activity. The insertion was located in the second codon of exon five and creates a frame-shift that generates a premature stop codon (FIG. 1). Seventeen haploid megagametophytes from the heterozygous 7-56 clone were assayed by isozyme gel electrophoresis and DNA sequence analysis to confirm the sequence mutation discovered was associated with CAD-deficiency. In every case, the two-base pair adenosine insertion corresponded with the absence of CAD activity (data not shown).

Genotyping of the cad-n1 Mutation by FP-TDI

Figure 3:
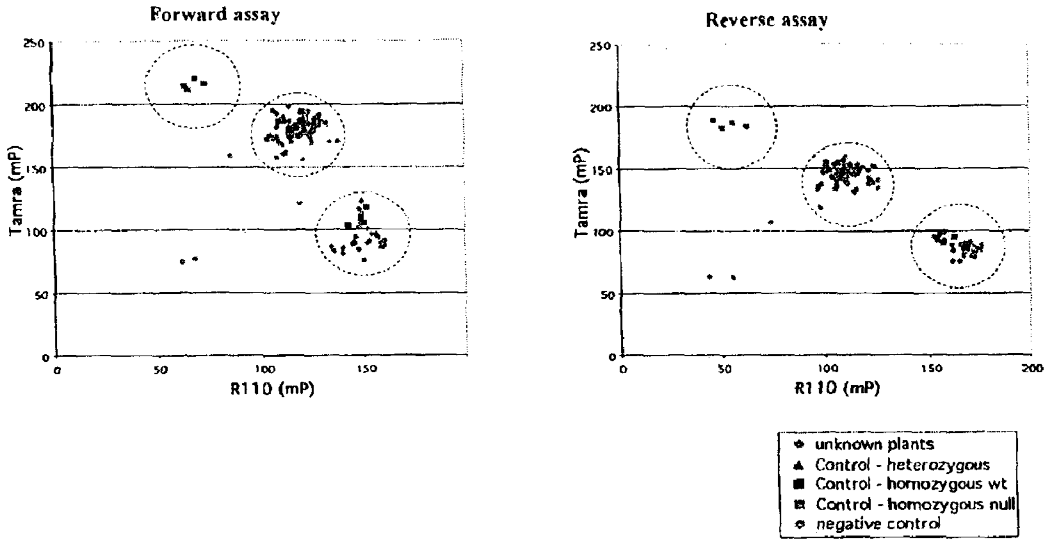
FIG. 3 shows the detection of the cad-n1 sequence mutation in 96 samples analyzed by the forward and reverse Template-directed Dye-terminator Incorporation and Fluorescence Polarization detection (FP-TDI) assay. Plants are grouped as control (heterozygous), control (homozygous wild type), control (homzygous null), negative controls and unknown plants.

Design of the forward and reverse FP-TDI assays are shown in FIG. 2. Trial testing of the assay was performed on 167 plants obtained from nine different crosses involving clone 7-56 or progeny from 7-56. Results from a subset of 96 plants using the forward and reverse FP-TDI assay are shown in FIG. 3. Controls were included that consisted of all three possible genotype classes and blanks that contained no DNA. Samples that did not fall clearly into a genotype cluster (1–2%) were not scored. When both the forward and reverse reaction results were combined, all plants were accurately assigned to a genotype class and no contradictory genotypes were observed. The absence of homozygous cad-n1 clones was expected based on the parental genotypes used to construct the nine crosses tested.

Analyzing an indel mutation by single-base extension has the potential for giving a false result if a substitution occurs in the position examined (FIG. 2). For example, if the first nucleotide of codon 241 (G) is substituted to an adenosine (forward assay) or the first base of codon 240 (G) is substituted to an adenosine (reverse assay) a false positive result for the cad-n1 allele would occur. Both of these positions require nonsynonymous amino acid changes to occur, alanine to threonine in the forward and glutamine to lysine in the reverse. These nonsynonymous changes were not observed in any of the clones present on the SNP discovery panel or in a selection of 242 first-generation clones. If both the forward and reverse assay are performed, the probability of an error occurring due to nucleotide substitutions would be extremely low.

Since the FP-TDI assay is based on single-base extension it should be amenable to other platforms such as the SureScore SNP Genotyping Kit (Invitrogen, Carlsbad, Calif., USA) and SNaPSHOT (Applied Biosystems, Foster City, Calif., USA).

SureScore, an integrated system that requires no specialized instrumentation, makes accessible genomic analysis tools that have traditionally been out of reach for many laboratories. The SureScore Kit includes primer design software, a 96-well assay kit, and data analysis software. The primer design software is used to design amplication and SNP-IT capture primers. The kit allows for genotyping to be conducted on up to 96 samples per SureScore strip-well plate, and commonly available equipment such as a 96-well plate washer and reader can be accommodated. Once the assay is completed, the kit provides data analysis software to interpret experimental results The single base extension reaction for the FP-TDI assay utilizes an internal extension primer, which is designed so that its 3' end anneals adjacent to the polymorphic base-pair. The reaction is essentially a sequencing reaction containing only dye-terminator nucleotides. Since there are no typical nucleotides, all that can occur is the addition of a single fluorescently-labeled dideoxynucleotide (F-ddNTP), which then cannot be extended further. In the FP-TDI assay, the identity of the base added (or bases if a heterozygote) will be discerned via measuring fluorescence polarization.

Primers and dNTPs left over from the original PCR are removed or degraded before running the singe-base extension reaction. Residual PCR primers are problematic because they can compete with the extension primer, effectively extending multiple targets, which would ruin the results. Residual dNTPs are problematic because they can allow extension to proceed beyond a single base.

The SNaPSHOT® system works by single base extension and then gel electrophoresis on a sequencer such as those provided by ABI.

Frequency of the cad-n1 Allele

Frequency of the cad-n1 allele was estimated by analyzing the 242 first generation clones that were distributed across the present-day range of loblolly pine (from Texas to Florida and extending north to Delaware). The mutation was not detected in any of the clones analyzed using the forward FP-TDI assay, confirming the rareness of this mutation. The frequency of cad-n1 might be higher in some populations, such as in the region where 7-56 was discovered (Williamsburg, N.C., USA), however much more extensive sampling would be required.

The frequency of cad-n1 in loblolly pine breeding populations and plantations will likely increase due to the inclusion of 7-56 as an elite parent in numerous co-operative and private breeding programmes. The diagnostic tool presented here will allow breeders to rapidly screen for the presence of the cad-n1 allele in their germplasm. Screening of additional loblolly pine populations could be performed to identify new select trees harboring the cad-n1 allele.

REFERENCES

The following references cited herein are hereby incorporated by reference in their entirety.

Baucher, M., Chabbert, B., Pilate, G., Van Doorsselaere, J., Tollier, M., Petit-Conil, M., Cornu, D., Monties, B., Van Montagu, M., Inze, D., Jouanin, L., and Boerjan, W. (1996) Red xylem and higher lignin extractibility by down-regulating a cinnamyl alcohol dehydrogenase in poplar. *Plant Physiol.* 112, 1479–1490

Dimmel, D. R., MacKay, J. J., Althen, E. M., Parks, C. J., and Sederoff, R. R. (2001) Pulping and bleaching of CAD-deficient wood. *J. Wood Chem. Technol.* 21, 1–17.

Dimmel, D. R., MacKay, J. J., Courchene, C., Kadla, J., Scott, J. T., O'Malley, D. M., and McKeand, S. E. (2002) Pulping and bleaching of partially CAD-deficient wood. *J. Wood Chem. Technol.* 22, 235–248.

Groover, A., Devey, M., Lee, J., Megraw, R. and Mitchell-Olds, T. (1994) Identification of quantitative trait loci influencing wood specific gravity in an outbred pedigree of loblolly pine. *Genetics* 138, 1293–1300

Hsu, T. M., Chen, X., Duan, S., Miller, R. D., and Kwok, P. Y. (2001) Universal SNP genotyping assay with fluorescence polarization detection. *Biotechniques* 31, 560–570 (2001)

Hu, W. J., Harding S. A., Lung, J., Popko, J. L., Ralph, J., Stokke, D. D., Tsai, C. J., and Chiang, V. L. (1999) Repression of lignin biosynthesis promotes cellulose accumulation and growth in transgenic trees. *Nat. Biotechnol.* 17, 808–812

Kwok, P. Y. (2002) SNP genotyping with fluorescence polarization detection. *Human Mutation* 19, 315–323

Lapierre, C., Pollet, B., MacKay, J. J., and Sederoff, R. R. (2000) Lignin structure in a mutant pine deficient in cinnamyl alcohol deydrogenase. *J. Agric. Food Chem.* 48,2326–2331

MacKay, J. J., Liu, W., Whetten, R., Sederoff, R. R., and O'Malley, D. M. (1995) Genetic analysis of cinnamyl alcohol-dehydrogenase in loblolly pine: single gene inheritance, molecular characterization and evolution. *Mol. Gen. Genet.* 247, 537–545

MacKay, J., O'Malley, D. M., Presnell, T., Booker, F. L., Campbell, M. M., Whetten, R. W., and Sederoff, R. R. (1997) Inheritance, gene expression, and lignin characterisation in a mutant pine deficient in cinnamyl alcohol dehydrogenase. *Proc. Natl. Acad. Sci. USA* 94, 8255–8260

Pilate, G., Guiney, E., Holt, K., Petit-Conil, M., Lapierre, C., Leple, J., Pollet, B., Mila, I., Webster, E. A., Marstorp, H. G., Hopkins, D. W., Jouanin, L., Boerjan, W., Schuch, W., Cornu, D., and Halpin, C. (2002) Field and pulping performances of transgenic trees with altered lignification. *Nat. Biotechnol.* 20, 607–612.

Ralph, J., MacKay, J. J., Hatfield, R. D., O'Malley, D. M., Whetten, R. W., and Sederoff, R. R. (1997) Abnormal lignin in a loblolly pine mutant. *Science* 277, 235–239

Vanin, E. F. (1985) Processed pseudogenes: characteristics and evolution. *Annu. Rev. Genet.* 19, 253–272

Wu, R. L., Remington, D. L., MacKay, J. J., McKeand, S. E., and O'Malley, D. M. (1999) Average effect of a mutation in lignin biosynthesis in loblolly pine. *Theor. Appl. Genet.* 99, 705–710

MacKay, J. J., Liu, W., Whetten, R., Sederoff, R. R., and O'Malley, D. M. (1995) Genetic analysis of cinnamyl alcohol dehydrogenase in loblolly pine: single gene inheritance, molecular characterization and evolution. *Mol. Gen. Genet.* 247, 537–545

MacKay, J., O'Malley, D. M., Presnell, T., Booker, F. L., Campbell, M. M., Whetten, R. W., and Sederoff, R. R. (1997) Inheritance, gene expression, and lignin characterisation in a mutant pine deficient in cinnamyl alcohol dehydrogenase. *Proc. Natl. Acad. Sci. USA* 94, 8255–8260

Pilate, G., Guiney, E., Holt, K., Petit-Conil, M., Lapierre, C., Leple, J., Pollet, B., Mila, I., Webster, E. A., Marstorp, H. G., Hopkins, D. W., Jouanin, L., Boerjan, W., Schuch, W., Cornu, D., and Halpin, C. (2002) Field and pulping performances of transgenic trees with altered lignification. *Nat. Biotechnol.* 20, 607–612.

Ralph, J., MacKay, J. J., Hatfield, R. D., O'Malley, D. M., Whetten, R. W., and Sederoff, R. R. (1997) Abnormal lignin in a loblolly pine mutant. Science 277, 235–239

Wu, R. L., Remington, D. L., MacKay, J. J., McKeand, S. E., and O'Malley, D. M. (1999) Average effect of a mutation in lignin biosynthesis in loblolly pine. *Theor. Appl. Genet.* 99, 705–710.

We claim:

1. A method of identifying a loblolly pine tree harboring a null CAD allele (cad-n1) wherein said loblolly pine tree contains a cad gene and said cad gene has a fifth exon, comprising:

identifying a loblolly pine tree containing a two base pair adenosine insertion in the fifth exon of said cad gene wherein the DNA sequence of said fifth exon comprising said two base pair adenosine insertion comprises the nucleotide sequence depicted in SEQ ID NO:3 or the complement thereof wherein the presence of SEQ ID NO:3 indicates a loblolly pine tree harboring a null CAD allele (cad-n1).

2. The method of claim 1 wherein said identifying is performed on a sample isolated from a pine tree, a pine tree seedling, a pine tree tissue culture, a pine tree cell culture or a pine tree megagametophte.

3. The method of claim 1 wherein said identifying is performed on a sample from pine bark, pine needle, pine tissue or pine seed.

4. The method of claim 1 wherein said two base pair adenosine insertion is identified by DNA sequencing.

5. The method of claim 1 wherein said two base pair adenosine insertion is identified by PCR.

6. The method of claim 1 wherein said two base pair adenosine insertion is identified by a single pair extension assay.

7. The method of claim 1 wherein the single base pair extension assay is template-directed dye-terminator incorporation and fluorescence polarization detection (FP-TDI).

8. The method of claim 7 wherein said FP-TDI includes the use of oligonucleotides wherein the sequences of said oligonucleotides consist of SEQ ID NO:13 or SEQ ID NO:14.

9. A method of selecting a loblolly pine tree harboring a null CAD allele (cad-n1) wherein said loblolly pine tree contains a cad gene and said cad gene has a fifth exon comprising:

a) providing a sample comprising DNA from said loblolly pine tree wherein said DNA comprises said cad gene;

b) determining whether said fifth exon comprises a two base pair adenosine insertion wherein the nucleotide sequence of the fifth exon comprising said two base pair adenosine insertion comprises the nudeotide sequence depicted in SEQ ID NO:3 or the complement thereof and c) selecting a loblolly pine tree harboring a null CAD allele (cad-n1)

wherein the presence of SEQ ID NO:3 is indicative of a loblolly pine tree harboring a null CAD allele (cad-n1).

10. The method of claim 9 wherein said determining is performed on a sample isolated from a pine tree, a pine tree seedling, a pine tree tissue culture sample, a pine tree cell culture sample or a pine tree megagmetophte.

11. The method of claim 9 wherein said identifying is performed on a sample from pine bark, pine needle, pine tissue or pine seed.

12. The method of claim 9 wherein said two base pair adenosine insertion is identified by DNA sequencing.

13. The method of claim 9 wherein said two base pair adenosine insertion is identified by PCR.

14. The method of claim 9 wherein said two base pair adenosine insertion is identified by a single pair extension assay.

15. The method of claim 14 wherein the single base pair extension assay is a template-directed dye-terminator incorporation and fluorescence polarization detection (FP-TDI) assay.

16. The method of claim 15 wherein said FP-TDI includes the use of at least two oligonucleotides wherein the sequences of said oligonucleotides consist of SEQ ID NO:13 and SEQ ID NO:14.

17. A method of identifying a loblolly pine tree harboring a null CAD allele (cad-n1), comprising:

a) providing a sample comprising DNA from said loblolly pine tree wherein said DNA contains a cad gene and said cad gene has a fifth exon;

b) performing template-directed dye-terminator incorporation and fluorescence polarization detection (FP-TDI) on said DNA to determine whether said fifth exon in said sample contains a two base pair adenosine insertion wherein the nucleotide sequence of the fifth exon containing said two base pair adenosine insertion comprises the nucleotide sequence depicted in SEQ ID NO:3 or the complement thereof c) identifying a sample containing said two base pair adenosine insertion in said cad gene wherein the presence of SEQ ID NO: 3 indicates a loblolly pine tree harboring a null CAD allele (cad-n1).

18. The method of claim 17 wherein said sample comprising DNA is amplified DNA wherein said DNA is amplified by PCR using two PCR primers wherein the sequence of said PCR primers consists of SEQ ID NO:11 and SEQ ID NO:12.

19. The method of claim 17 wherein said FP-TDI is performed utilizing two primers wherein the sequence of said primers consists of SEQ ID NO:13 and SEQ ID NO:14.

20. The method of claim 17 wherein said sample is isolated from a pine tree, a pine tree seedling, a pine tree tissue culture sample, a pine tree cell culture or a pine tree megagametophte.

21. The method of claim 17 wherein said FP-TDI is performed on a sample from pine bark, pine needle, pine tissue or pine seed.

22. A method of identifying a loblolly pine tree harboring a null CAD allele (cad-n1), comprising:

a) providing a sample comprising DNA from said loblolly pine tree wherein said DNA contains a cad gene and said cad gene has a fifth exon wherein said DNA in said sample is amplified by PCR using PCR primers wherein the sequences of said primers consists of SEQ ID NO:11 and SEQ ID NO: 12;

b) performing template-directed dye-terminator incorporation and fluorescence polanzation detection (FP-TDI) on said DNA using oligonucleotides having nucleotide sequences consisting of SEQ ID NO:11 and SEQ ID NO:12 to determine whether said fifth exon of the cad gene in said sample contains a two base pair adenosine insertion wherein the nucleotide sequence of the fifth exon containing said two base pair adenosine insertion comprises the nucleotide sequence depicted in SEQ ID NO:3 wherein said two base pair adenosine insertion is indicative of a pine tree harboring the null CAD allele (cad-n1) and c) identifying a loblolly pine tree harboring a null CAD allele (cad-n1)

wherein the presence of SEQ ID NO: 3 is indicative of a loblolly pine tree harboring a null CAD allele (cad-n1).

23. The method of claim 22 wherein said sample is isolated from a pine tree, a pine tree seedling, a pine tree tissue culture sample, a pine tree cell culture or a pine tree megagametophte.

24. The method of claim 22 wherein said identifying is performed on a sample from pine bark, pine needle, pine tissue or pine seed.

25. A method of identifying a loblolly pine tree homozygous for the null CAD allele (cad-n1/cad-n1) wherein said pine tree contains a cad gene and said cad gene has a fifth exon, comprising:

identifying a loblolly pine tree, wherein said loblolly pine tree contains DNA with a two base pair adenosine insertion in the fifth exon of said cad gene wherein the DNA sequence of said fifth exon comprising said two base pair adenosine insertion comprises the nucleotide sequence depicted in SEQ ID NO:3 or the complement thereof wherein said pine tree does not contain DNA with wild type sequence for the fifth exon of said cad gene wherein the wildtype sequence is depicted in SEQ ID NO:1 or the complement thereof wherein the presence of SEQ ID NO: 3 and the absence of SEQ ID NO: 1 indicates a loblolly pine tree homozygous for the null CAD allele (cad-n1/cad-n1).

26. The method of claim 25 wherein said identifying is performed on a sample isolated from a pine tree, a pine tree seedling, a pine tree tissue culture, a pine tree cell culture or a pine tree megagametophte.

27. The method of claim 25 wherein said identifying is performed on a sample from pine bark, pine needle, pine tissue or pine seed.

28. The method of claim 25 wherein said two base pair adenosine insertion is identified by DNA sequencing.

29. The method of claim 25 wherein said two base pair adenosine insertion is identified by PCR.

30. The method of claim 25 wherein said two base pair adenosine insertion is identified by a single pair extension assay.

31. The method of claim 30 wherein the single base pair extension assay is template-directed dye-terminator incorporation and fluorescence polarization detection (FP-TDI).

32. The method of claim 31 wherein said FP-TDI includes the use of oligonucleotides wherein the sequences of said oligonucleotides consist of SEQ ID NO:13 or SEQ ID NO:14.

33. A method of identifying a loblolly pine tree heterozygous for the null CAD allele (cad/cad-n1) wherein said pine tree contains a cad gene and said cad gene has a fifth exon, comprising:

identifying a loblolly pine tree comprising DNA with a two base pair adenosine insertion in the fifth exon of said cad gene wherein the DNA sequence of said fifth exon comprising said two base pair adenosine insertion comprises the nucleotide sequence depicted in SEQ ID NO:3 or the complement thereof and identifying said loblolly pine tree as also comprising the wild type sequence for the fifth exon of said cad gene wherein the wild type sequence is depicted in SEQ ID NO:1 or the complement thereof wherein the presence of both SEQ ID NO: 3 and SEQ ID NO: 1 indicates a loblolly pine tree heterozygous for the null CAD allele (cad/cad-n1).

34. The method of claim 33 wherein said identifying is performed on a sample isolated from a pine tree, a pine tree seedling, a pine tree tissue culture, a pine tree cell culture or a pine tree megagametophte.

35. The method of claim 33 wherein said identifying is performed on a sample from pine bark, pine needle, pine tissue or pine seed.

36. The method of claim 33 wherein said two base pair adenosine insertion is identified by DNA sequencing.

37. The method of claim 33 wherein said two base pair adenosine insertion is identified by PCR.

38. The method of claim 33 wherein said two base pair adenosine insertion is identified by a single pair extension assay.

39. The method of claim 38 wherein the single base pair extension assay is template-directed dye-terminator incorporation and fluorescence polarization detection (FP-TDI).

40. The method of claim 39 wherein said FP-TDI includes the use of oligonucleotides wherein the sequences of said oligonucleotides consist of SEQ ID NO:13 or SEQ ID NO:14.

41. A method of identifying a loblolly pine tree homozygous for the wild type CAD allele (cad/cad) wherein sad pine tree contains a cad gene and said cad gene has a fifth exon, comprising:

identifying a loblolly pine tree comprising DNA with wild type sequence for the fifth exon of said cad gene wherein the wildtype sequence is depicted in SEQ ID NO:1 or the complement thereof wherein said loblolly pine tree does not contain DNA with a two base pair adenosine insertion in the fifth exon of said cad gene wherein the DNA sequence of said fifth exon comprising said two base pair adenosine insertion comprises the nucleotide sequence depicted in SEQ ID NO:3 or the complement thereof wherein the presence of SEQ ID NO: 1 and absence of SEQ ID NO: 3 indicates a loblolly pine tree homozygous for the wild type CAD allele (cad/cad).

42. The method of claim 41 wherein said identifying is performed on a sample isolated from a pine tree, a pine tree seedling, a pine tree tissue culture, a pine tree cell culture or a pine tree megagametophte.

43. The method of claim 41 wherein said identifying is performed on a sample from pine bark, pine needle, pine tissue or pine seed.

44. The method of claim 41 wherein said two base pair adenosine insertion is identified by DNA sequencing.

45. The method of claim 41 wherein said two base pair adenosine insertion is identified by PCR.

46. The method of claim 41 wherein said two base pair adenosine insertion is identified by a single pair extension assay.

47. The method of claim 46 wherein the single base pair extension assay is template-directed dye-terminator incorporation and fluorescence polarization detection (FP-TDI).

48. The method of claim 47 wherein said FP-TDI includes the use of oligonucleotides wherein the sequences of said oligonucleotides consist of SEQ ID NO:13 or SEQ ID NO:14.

* * * * *

SEQUENCE LISTING

```
<160> NUMBER OF SEQ ID NOS: 14

<210> SEQ ID NO 1
<211> LENGTH: 33
<212> TYPE: DNA
<213> ORGANISM: Pinus taeda

<400> SEQUENCE: 1

gaagcagcag agagcctaga ttacataatg gac                                  33


<210> SEQ ID NO 2
<211> LENGTH: 11
<212> TYPE: PRT
<213> ORGANISM: Pinus taeda

<400> SEQUENCE: 2

Glu Ala Ala Glu Ser Leu Asp Tyr Ile Met Asp
 1               5                  10


<210> SEQ ID NO 3
<211> LENGTH: 35
<212> TYPE: DNA
<213> ORGANISM: Pinus taeda

<400> SEQUENCE: 3

gaaaagcagc agagagccta gattacataa tggac                                35


<210> SEQ ID NO 4
<211> LENGTH: 6
<212> TYPE: PRT
<213> ORGANISM: Pinus taeda

<400> SEQUENCE: 4

Glu Lys Gln Gln Arg Ala
 1               5


<210> SEQ ID NO 5
<211> LENGTH: 18
<212> TYPE: DNA
<213> ORGANISM: Pinus taeda

<400> SEQUENCE: 5
```

-continued gaagcagcag agagccta 18

<210> SEQ ID NO 6
<211> LENGTH: 18
<212> TYPE: DNA
<213> ORGANISM: Pinus taeda

<400> SEQUENCE: 6
taggctctct gctgcttc 18

<210> SEQ ID NO 7
<211> LENGTH: 21
<212> TYPE: DNA
<213> ORGANISM: Pinus taeda

<400> SEQUENCE: 7
gaaaagcagc agagagccta g 21

<210> SEQ ID NO 8
<211> LENGTH: 21
<212> TYPE: DNA
<213> ORGANISM: Pinus taeda

<400> SEQUENCE: 8
ctaggctctc tgctgctttt c 21

<210> SEQ ID NO 9
<211> LENGTH: 24
<212> TYPE: DNA
<213> ORGANISM: Artificial Sequence
<220> FEATURE:
<223> OTHER INFORMATION: Forward Primer

<400> SEQUENCE: 9
cctctgttat gtgcaggggt taca 24

<210> SEQ ID NO 10
<211> LENGTH: 19
<212> TYPE: DNA
<213> ORGANISM: Artificial Sequence
<220> FEATURE:
<223> OTHER INFORMATION: Reverse Primer

<400> SEQUENCE: 10
cgaagtgcaa cggctctgg 19

<210> SEQ ID NO 11
<211> LENGTH: 21
<212> TYPE: DNA
<213> ORGANISM: Artificial Sequence
<220> FEATURE:
<223> OTHER INFORMATION: Forward Primer

<400> SEQUENCE: 11
tgaaaagatg atgtgcgcca a 21

<210> SEQ ID NO 12
<211> LENGTH: 19
<212> TYPE: DNA
<213> ORGANISM: Artificial Sequence
<220> FEATURE:
<223> OTHER INFORMATION: Reverse Primer

<400> SEQUENCE: 12
cgaagtgcaa cggctctgg 19

-continued

```
<210> SEQ ID NO 13
<211> LENGTH: 19
<212> TYPE: DNA
<213> ORGANISM: Artificial Sequence
<220> FEATURE:
<223> OTHER INFORMATION: Forward Primer

<400> SEQUENCE: 13

atccgttgtg ttgcaggaa                                                     19


<210> SEQ ID NO 14
<211> LENGTH: 23
<212> TYPE: DNA
<213> ORGANISM: Artificial Sequence
<220> FEATURE:
<223> OTHER INFORMATION: Reverse Primer

<400> SEQUENCE: 14

gtaatctagg ctctctgctg ctt                                                23
```